United States Patent

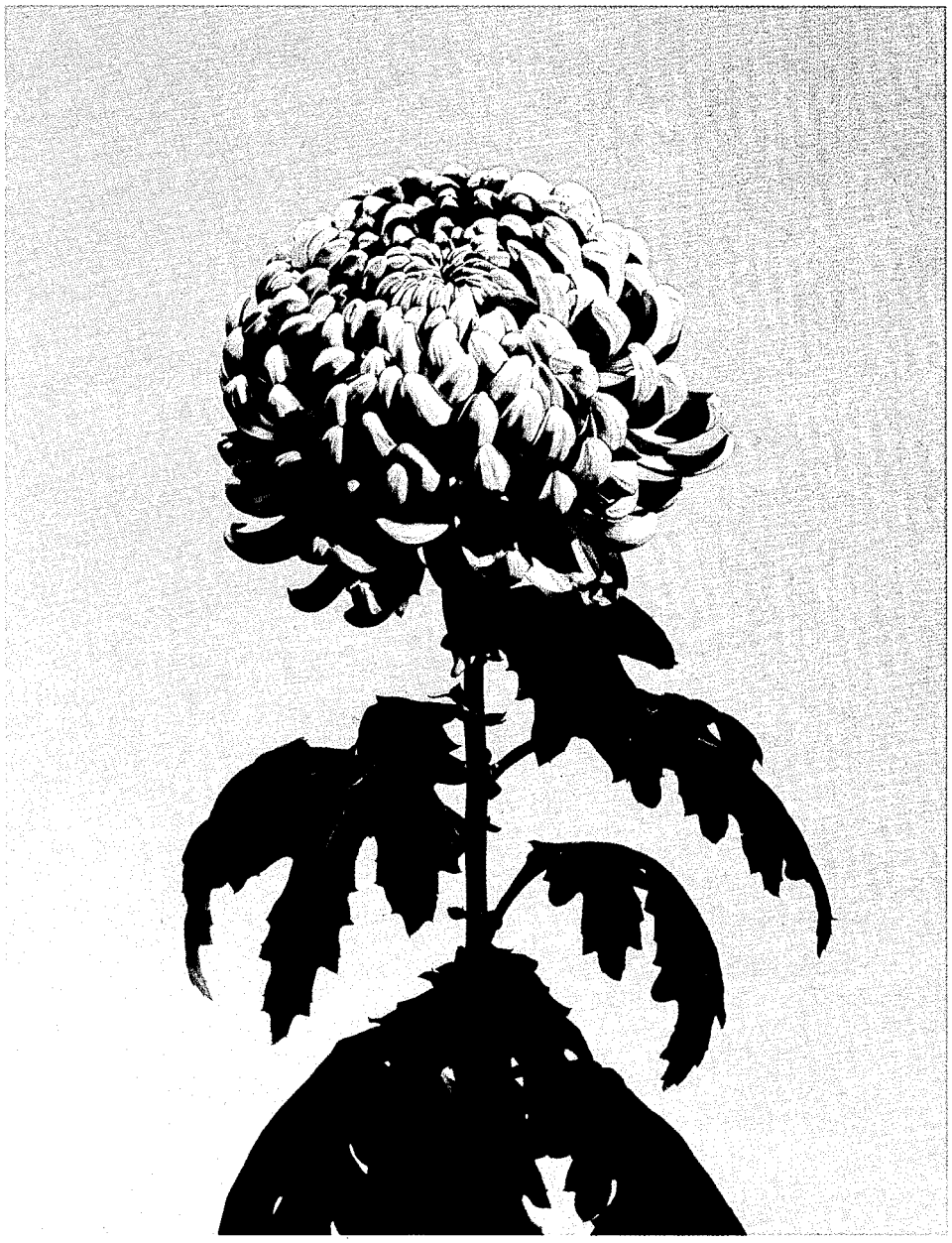

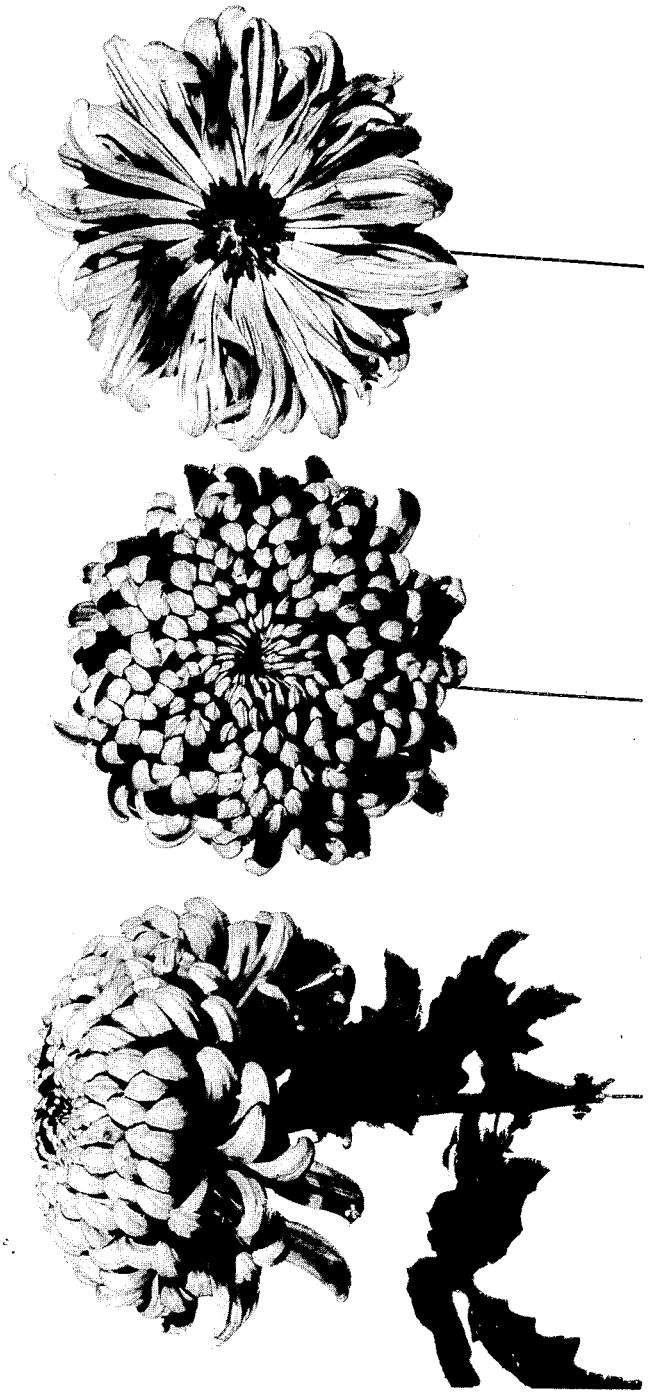

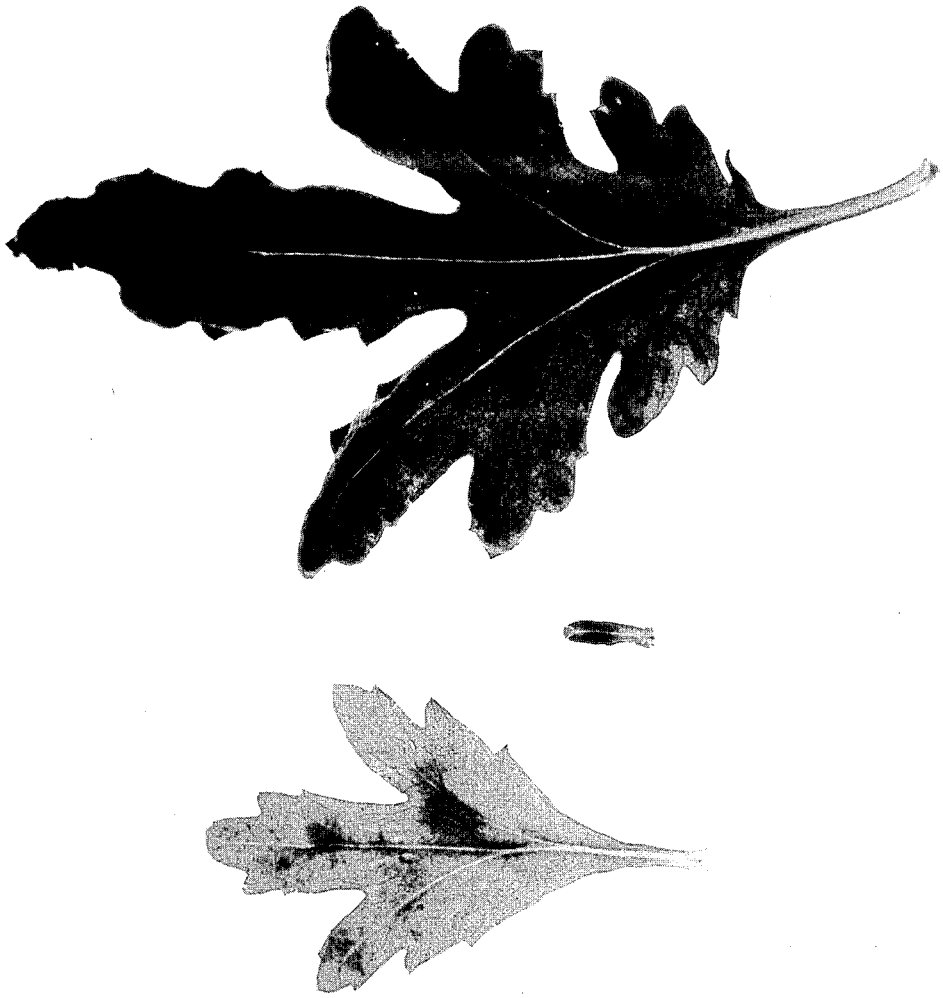

Plant Pat. 3,890

Patented May 18, 1976

3,890

CHRYSANTHEMUM PLANT

Walter H. Jessel, Jr., Doylestown, and William Erwin Duffett, Akron, Ohio, assignors to Yoder Brothers, Inc., Barberton, Ohio

Filed Apr. 16, 1975, Ser. No. 568,569

Int. Cl. A01h *5/00*

U.S. Cl. Plt.—76 1 Claim

The present invention comprises a new and distinct cultivar of *Chrysanthemum morifolium*, Ramat., hereinafter referred to by the cultivar name Burgandy (#71219001).

Burgandy was originated from a cross made in a controlled breeding program in Barberton, Ohio in the year 1970. The female, or seed parent, was #63645002 (unnamed seedling), a pink standard originated by the present inventors from a cross between George Ingham (#22018E01; unpatented; commercially available) and #22018E02 (unnamed seedling). George Ingham is of parentage unknown to the present inventors. #22018E02 is a product of the breeding program of the present inventors.

The male, or pollen parent of Burgandy, was #70125001 (unnamed seedling), a pink standard originated by the present inventors from a cross between #621003-1 (unnamed seedling) and #68029002 (unnamed seedling). Both #621003-1 and #68029002 are products of the breeding program of the present inventors.

Burgandy was discovered and selected as a flowering seedling within the progeny of the stated cross by William E. Duffett and Walter H. Jessel, Jr. on Dec. 1, 1971 in a controlled environment in Barberton, Ohio.

Burgandy is a product of a planned breeding program which had the objective of creating incurved standards adaptable to commercial single stem pot and cut programs with durable foliage, uniform nine week response, uniform gradeout (SAF standards), and intense inflorescence color. These traits in combination were not present in previously available commercial cultivars.

The first act of asexual reproduction of Burgandy was accomplished when vegetative cuttings were taken from the initial selection in February 1972 in a controlled environment in Barberton, Ohio by a technician working under formulations established and supervised by William E. Duffett and Walter H. Jessel, Jr. Horticultural examination of selected units initialed Dec. 1, 1972, has demonstrated that the combination of characteristics as herein disclosed for Burgandy are firmly fixed and are retained through successive generations of asexual reproduction.

Burgandy has not been observed under all possible environments. The phenotype may vary significantly with variations in environment such as temperature, light intensity, and daylength. The following observations, measurements, and comparisons describe single stem, disbudded plants grown in a greenhouse in Barberton, Ohio under environmental conditions which approximate those generally used in commercial practice, as described in Chart A and Chart B which appear at the end of the present specification.

The following traits have been repeatedly observed and are determined to be basic characteristics of Burgandy which in combination distinguish this chrysanthemum as a new and distinct cultivar:

(1) Standard inflorescence type.
(2) Incurved inflorescence form.
(3) Diameter across face of inflorescence from 5–6 inches at maturity.
(4) Purple abaxial ray floret color with lavender adaxial color.
(5) Tall plant height.
(6) Semi-upright branching habit.
(7) Uniform nine week flowering response period.
(8) Durable, leathery textured foliage.
(9) Uniform gradeout (SAF standards).

The accompanying photographic drawings show typical inflorescence and foliage characteristics of Burgandy, with colors being as nearly true as possible with illustrations of this type. While the actual inflorescence color of Burgandy is closely approximated in Sheet 1, the representation of foliage color is inaccurate, with the foliage colors, however, being accurately set forth in the color values which appear below. Sheet 2 is a black and white photograph showing three views of the inflorescence of Burgandy, and Sheet 3 is a black and white photograph of the foliage of Burgandy at three stages of growth.

Of the many commercial cultivars known to the present inventors, the most similar existing cultivars in comparison to Burgandy are Deep Champagne (#58176A01; U.S. Plant Pat. #3,300), #4 Improved Indianapolis Pink (#21032P01; unpatented), and Promenade (#64207-A01; U.S. Plant Pat. #3,221). Reference is made to attached Chart C which compares certain characteristics of the above mentioned cultivars with the same characteristics of Burgandy. General comparisons are as follows:

(1) In comparison to Deep Champagne, Burgandy has darker ray floret color, larger diameter across face of inflorescence, more uniform gradeout (SAF standards), taller plant height, shorter flowering response period, and more incurved inflorescence form. The branching habit and inflorescence type of Burgandy are similar to those of Deep Champagne.

(2) In comparison to #4 Improved Indianapolis Pink, Burgandy has darker ray floret color, smaller diameter across face of inflorescence, and more uniform gradeout (SAF standards). The plant height, branching habit, flowering response period, and inflorescence form and type of Burgandy are similar to those of #4 Improved Indianapolis Pink.

II. Plant

A. General appearance: Tall; semi-upright.
B. Duration and texture: Herbaceous; perennial.
C. Foliage:
*Color (abaxial).*—Approximately 21–16.
*Color (adaxial).*—Approximately 21–14.
*Shape.*—Spatulate; deeply lobed.
*Texture.*—Glabrous; leathery.
*Arrangement.*—Alternate.
*Veination.*—Prominent.
*Margin.*—Deeply serrated.

CHART A—AVERAGE GREENHOUSE CHRYSANTHEMUM ENVIRONMENTS USED FOR BARBERTON, OHIO

| Season | Temperatures used (° F.) Night | Bright day | Cloudy day | Lighting used | Black cloth used | Supp., $CO_2$ |
|---|---|---|---|---|---|---|
| Fall | 65 to 56 | 65 to 80 | 60 to 75 | 2 to 4 weeks at 3 hours per night of 7–10 f.c. | To Sept. 15: on, 5:30 p.m.; off, 7:30 a.m. | From Oct. 15: 3000 p.p.m. |
| Winter | 58 to 62 | 65 to 70 | 60 to 65 | 2 to 5 weeks at 5 hours per night of 7–10 f.c. | None | 300 p.p.m. |
| Spring | 58 to 65 | 65 to 80 | 60 to 75 | 2 to 4 weeks at 5 hours per night of 7–10 f.c. | From Mar. 15: on, 5:30 p.m.; off, 7:30 a.m. | To Apr. 15: 300 p.p.m. |
| Summer | 62 to 68 | 70 to 90 | 65 to 75 | 1 to 2 weeks at 3 hours per night of 7–10 f.c. | On, 6:00 p.m.; off, 8:00 am. | None. |

NOTE.—For intensity of direct solar radiation, refer to Chart B.

(3) In comparison to Promenade, Burgandy has darker ray floret color, smaller diameter across face of inflorescence, and more incurved inflorescence form. The uniformity of gradeout (SAF standards), plant height, branching habit, flowering response period, and inflorescence type of Burgandy are similar to those of Promenade.

In the following description, color references are made to The Munsell Limit Color Cascade, 1972 edition. The color values were determined between 2:00 p.m. and 2:30 p.m. on Mar. 11, 1975 under 160 foot candle light intensity.

Botanical classification: *Chrysanthemum morifolium*, Ramat., cv Burgandy

I. Inflorescence

A. Capitulum:
*Form.*—Incurve.
*Type.*—Standard.
*Permanence.*—14–18 days.
*Diameter across face.*—5.0 to 6.0 inches.
B. Corolla of ray florets:
*Texture (adaxial).*—Glabrous.

CHART B

INTENSITY OF DIRECT SOLAR RADIATION

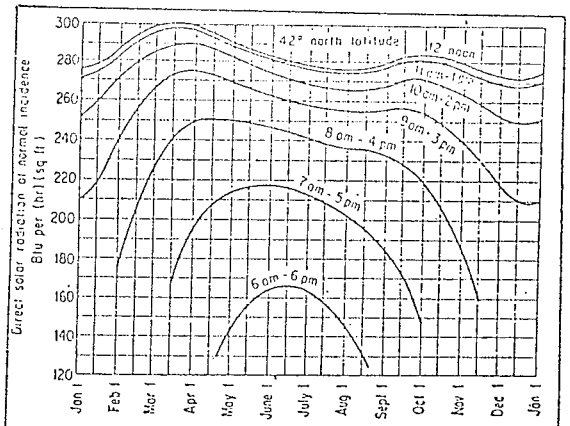

Figure 14.14 Intensity of direct solar radiation normal to the sun's rays at 42 degrees north latitude for an atmospheric clearness number of unity. (Reprinted by permission from *ASHAE Trans.*, Vol. 64, p. 64.)

CHART C—COMPARISON OF BURGANDY WITH DEEP CHAMPAGNE, #4 IMPROVED INDIANAPOLIS PINK AND PROMENADE

| Cultivar | Inflorescence color | Diameter across face of inflorescence (inches) | Grade-out SAF (standards) | Plant height | Branching habit | Flowering response period (weeks) | Inflorescence form and type |
|---|---|---|---|---|---|---|---|
| Burgandy | Purple with lavender reverse. | 5.0 to 6.0 | Uniform | Tall | Semi-upright | 9 | Incurve standard. |
| Deep Champagne | Lavender | 4.75 to 5.75 | Uneven | Medium | do | 11 | Semi-incurve standard. |
| #4 Improved Indianapolis Pink. | Dark lavender with lavender reverse. | 5.5 to 6.5 | do | Tall | do | 9 | Incurve standard. |
| Promenade | Dark lavender | 5.75 to 6.5 | Uniform | do | do | 9 | Semi-incurve standard. |

Comparisons made of plants grown in a greenhouse in Barberton, Ohio under conditions described in Charts A and B.

*Appearance and form.*—Ligulate.
*Arrangement.*—Whorled on receptacle.
*Persistence.*—Resists shatter.
*Color (abaxial).*—44–12 to 44–13 streaked with 44–14.
*Color (adaxial).*—44–12 over white.
C. Reproductive organs:
*Androecium.*—Scant; present disc florets only; syngenesious stamen; scant to no pollen.
*Gynoecium.*—Present both ray and disc florets; inferior, bicarpellate ovary; single style; 2-lobed stigma.

We claim:

1. A new and distinct cultivar of Chrysanthemum plant characterized particularly by uniqueness in the combined characteristics of standard inflorescence type, incurved inflorescence form, 5 to 6 inch diameter across face of inflorescence at maturity, purple abaxial ray floret color with lavender adaxial color, tall plant height, semi-upright branching habit, uniform nine week flowering response period, durable leathery textured foliage, and uniform gradeout.

No references cited.

ROBERT E. BAGWILL, Primary Examiner